(12) United States Patent
Rogers et al.

(10) Patent No.: US 7,183,424 B1
(45) Date of Patent: Feb. 27, 2007

US007183424B1

(54) SHEA BUTTER ALKANOLAMIDES

(75) Inventors: Steven Rogers, Yardley, PA (US);
Anthony O'Lenick, Jr., Dacula, GA (US)

(73) Assignee: Rutherford Chemicals, LLC, Bayonne, NJ (US)

( * ) Notice: Subject to any disclaimer, the term of this patent is extended or adjusted under 35 U.S.C. 154(b) by 0 days.

(21) Appl. No.: 11/347,260

(22) Filed: Feb. 6, 2006

(51) Int. Cl.
*C07C 231/00* (2006.01)

(52) U.S. Cl. .......................................... 554/69; 554/64
(58) Field of Classification Search .................. 554/69, 554/66

See application file for complete search history.

*Primary Examiner*—Deborah D. Carr
(74) *Attorney, Agent, or Firm*—Louis C. Paul, ESQ

(57) ABSTRACT

Novel alkanolamides prepared by the reaction of an alkanolamine and shea butter, preferably mild-processed shea butter (MPSB). Materials of the present invention are useful as cosmetic and personal care ingredients; they thicken shampoos and body washes, stabilize foam, and deliver to the hair and skin highly desirable unsaponifiables present in shea butter, including natural antioxidants.

32 Claims, No Drawings

SHEA BUTTER ALKANOLAMIDES

CROSS-REFERENCE TO RELATED APPLICATIONS

Not applicable.

STATEMENT REGARDING FEDERALLY-SPONSORED RESEARCH OR DEVELOPMENT

Not applicable.

FIELD OF THE INVENTION

The present invention relates to novel alkanolamides prepared by the reaction of an alkanolamine and shea butter, preferably mild-processed shea butter (MPSB). Materials of the present invention are useful as cosmetic and personal care ingredients; they thicken shampoos and body washes, stabilize foam, and deliver to the hair and skin highly desirable active ingredients present in shea butter, including natural antioxidants.

BACKGROUND OF THE INVENTION

Alkanolamides perform a variety of functions including viscosity enhancement, foam stabilization, emulsification and detergency. Specific applications include as humectants and hair detanglers. Chemically, alkanolamides are the reaction product of an alkanolamine and a fatty material. Fatty materials are a class of compounds which include fatty carboxylic acids, fatty methyl esters and fatty glycerides. Sources of fatty materials include coconut, peanut, soybean, and rapeseed oils, fractionated and non-fractionated fatty methyl esters and fatty acids of carbon chains of varying lengths.

Variations in carbon chain lengths of the fatty sources can change the properties of alkanolamides. For example, a finished product having as an ingredient $C_8$ to $C_{10}$ fatty acids exhibit foam stability, but contribute little as thickeners. $C_{12}$ to $C_{14}$ fatty acids are particularly useful as foam boosters; they also show good viscosity building properties. Blending alkanolamides of differing carbon chain lengths can help optimize performance of the finished products in which they are incorporated. Lauric-myristic diethanolamides, for example, are common ingredients in formulations of high foaming products such as dishwashing detergent, bubble bath and hair shampoo. They also impart emolliency and conditioning effects to skin and hair, making them among the most commonly used alkanolamides in the personal care industry.

Higher molecular weight, unsaturated fatty alkanolamides reduce foam and produce good viscosity build. Illustrative are oleic and linoleic alkanolamides which are excellent viscosity builders at low concentrations. This property makes them particularly useful in surfactant-containing formulations that otherwise are difficult to thicken. Higher molecular weight unsaturated products, however, are known to be oxidatively unstable and can interfere with fragrance in finished products.

Shea butter is a butter extracted from the kernel of *Butrospermum parkii*. This plant, also referred to as *Vitellaria paradoxa*, is native to Africa. The term butter describes a material that is a solid at room temperature, but melts at about 40° C. Chemically, shea butter is a triglyceride conforming to the following structure

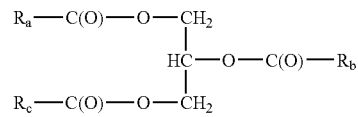

wherein $R_a$, $R_b$ and $R_c$ each have one of the following compositions:

| R Group | Common Name | Range (%) | Typical (%) |
|---|---|---|---|
| $C_{11}H_{23}$ | Lauryl | 0.1–2.0 | 0.2 |
| $C_{13}H_{27}$ | Myristyl | 0.5–2.0 | 1.0 |
| $C_{15}H_{31}$ | Cetyl | 2.0–6.0 | 4.0 |
| $C_{17}H_{35}$ | Stearyl | 25.0–50.0 | 35.0 |
| $C_{17}H_{33}$ | Oleyl | 40.0–60.0 | 59.0 |
| $C_{17}H_{31}$ | Linoleyl | 0.5–1.0 | 0.8 |

The average composition of $R_b$ is different than $R_a$ and $R_c$, the latter two being similar. The $R_b$ moiety contains predominantly the unsaturated $C_{18}$ group (oleyl) while $R_a$ and $R_c$ contain predominantly the saturated $C_{18}$ group (stearyl). Differences between internal ($R_b$) and terminal ($R_a$, $R_c$) substitution are seen in natural products but not in synthetic molecules produced in the laboratory.

The high levels of stearyl and oleyl groups make shea butter and its alkanolamide derivatives of particular interest in the personal care industry. While other raw materials used in personal care products have these species, the compounds of the present invention have significantly high concentrations of unsaponifiables, which posses highly desired antioxidant, ultra-violet radiation protection, and free-radical scavenging properties. MPSB of the present invention typically contains from about 5% to about 15% by weight of unsaponifiables. In contrast, other butters commonly used in personal care products have less than 2% unsaponifiables. For example, coca butter (from *Theobroma cacao*) averages 0.4% unsaponifiables and Illipe butter (from *Shorea stenoptera*) averages 1.1%.

As described in greater detail below, the novel shea butter alkanolamide compounds of the present invention are produced by reacting shea butter, preferably MPSB, with an alkanolamine, preferably under specific mild processing conditions. By "mild processed" is meant processes that do not remove or otherwise diminish the amount or potency of active ingredients, particularly highly desired unsaponifiables. In one aspect of the present invention, mild processing is employed both at the time of harvesting and initial extraction (creating mild-processed shea butter) and during subsequent preparation of derivatives. These mild processes result in materials containing unexpectedly high amounts unsaponifiables, notably antioxidants.

Prior art alkanolamides do not possess the antioxidant and free-radical scavenging properties of compounds of the present invention. For example, U.S. Pat. No. 5,741,916 discloses the use of meadowfoam seed oil to make alkanolamides. The materials described in the '916 patent do not possess the desirable unsaponifiable fractions which are present in the alkanolamides of the present invention.

The shea butter alkanolamides of the present invention thus deliver unexpectedly high amounts of unsaponifiables to the skin and hair in a heretofore unachievable manner. They not only thicken but also act as antioxidants and free radical scavengers.

SUMMARY OF THE INVENTION

The present invention relates to a novel class of alkanolamides made by reacting shea butter with alkanolamines and a process for using them in personal care applications. In a preferred aspect of the present invention, mild processing is employed both at the time of harvesting and initial extraction (creating mild-processed shea butter) and during subsequent preparation of alkanolamide derivatives. In so doing, materials containing unexpectedly high amounts of active ingredients, particularly highly desired unsaponifiables, are produced.

DETAILED DESCRIPTION OF THE INVENTION

The compounds of the present invention are alkanolamides produced by reacting shea butter with an alkanolamine. Preferably, the shea butter is mild-processed and is reacted with an alkanolamine under mild processing conditions. The novel alkanolamides of the present invention are rich in unsaponifiables, including antioxidants and free-radical scavengers.

Shea butter alkanolamide derivatives of the present invention conform to the following structure:

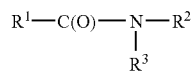

Wherein
(i) $R^1$ is derived from shea butter and comprises
   from about 0.1 to about 2.0% by weight $C_{13}H_{23}$;
   from about 0.5 to about 2.0% by weight $C_{13}H_{27}$;
   from about 2.0 to about 6.0% by weight $C_{15}H_{31}$;
   from about 25 to about 50% by weight $C_{17}H_{35}$; and
   from about 40.0 to about 60.0% by weight $C_{17}H_{33}$;
(ii) $R^2$ is selected from the group consisting of
   —$CH_2CH_2OH$, —$CH_2CH(CH_3)OH$ and
   —$CH_2CH_2OCH_2CH_2OH$; and
(iii) $R^3$ is selected from the group consisting of —H,
   —$CH_2CH_2OH$.

Shea Butter

Shea butter can be prepared by standard extraction techniques known to those of skill in the art. For example, U.S. Pat. No. 6,552,208, the disclosure of which is incorporated herein by reference, describes several methods for processing shea butter. Suitable extraction vehicles may include, but are not limited to, ethanol, methanol, ethyl acetate, acetone, chloroform and water, or any other solvent and water.

In a preferred aspect of the present invention, shea butter is mild-processed; it is extracted using a hydrocarbon-free solvent system and its alkanolamide derivatives are made under mild processing conditions. At the time of harvesting and initial extraction ground-up kernels are boiled in water under mild conditions as described in the examples below. The oil phase is then separated from the water phase by decanting. This process provides a yellow solid wax rich in unsaponifiables. By wax is meant a material obtained by boiling in water under ambient conditions, decanted and filtered.

The mild processing of the present invention may be contrasted with separation using solvents and high temperature treatment with high pressure steam. While the latter processes result in what some may describe as a "more pure" triglyceride, unsaponifiables, and the benefits derived therefrom, are lost. Vacuum distillation which strips off the desirable components is also to be avoided in processing MPSB of the present invention. By processing shea butter under mild conditions, materials comprising from about 5% to about 15% by weight of unsaponifiables can be produced.

Sterols comprise about 20% of the unsaponifiables in shea butter. More particularly, the sterols comprise: cholesterol (from about 1% to about 3%); alpha-spinasterol (from about 1% to about 4%); delta-7-stigmasterol (from about 40% to about 44%); delta-7-avenasterol (from about 38% to about 41%). The remaining constituents of the unsaponifiables (about 80%) include other highly desirable active compounds including tocopherol, karitin, cinamic acid esters, alpha and beta amyrin and phenolics.

Phenolic compounds are natural products composed of one or more aromatic benzene rings with one or more hydroxyl group. They are a class of natural products that possess antioxidant and free radical scavenging properties. Among the phenolics in the unsaponifiables of mild-processed shea butter include gallic acid, gallocatchin, catechin, epigallocatechin gallate, epicatechin, gallocatechin gallate, gallocatechin gallate and quercetin.

Alkanolamines

Alkanolamides of the present invention are made by the amidation reaction of shea butter (or, preferably, MPSB) with an alkanolamine conforming to the following structure:

wherein
(i) $R^2$ is selected from the group consisting of
   —$CH_2CH_2OH$, —$CH_2CH(CH_3)OH$ and
   —$CH_2CH_2OCH_2CH_2OH$; and
(ii) $R^3$ is selected from the group consisting of —H,
   —$CH_2CH_2OH$.

Alkanolamines suitable for use in the present invention are commercially available from a variety of suppliers, including Dow Chemical (Midland, Mich.). Illustrative examples of suitable alkanolamines are listed below:

| Example | $R^2$ | $R^3$ | Chemical Name |
|---|---|---|---|
| 1 | —$CH_2CH_2OH$ | —H | Monoethanolamine |
| 2 | —$CH_2CH_2OH$ | —$CH_2CH_2OH$ | Diethanolamine |
| 3 | —$CH_2CH_2O$—$CH_2CH_2OH$ | —H | Diglycolamine |
| 4 | —$CH_2CH(CH_3)OH$ | —H | Monoisopropanol amine |

In a preferred embodiment, the amidation is conducted at a temperature of from about 80° C. to about 90° C. in the presence of an anhydrous alkaline catalyst.

Another aspect of the present invention is a process for delivering antioxidants to the skin or hair by topically applying a finished product comprising an effective amount of an alkanolamide made by the amidation reaction of shea butter (or, preferably, MPSB) and an alkanolamine conforming to the following structure:

wherein
(i) $R^2$ is selected from the group consisting of $-CH_2CH_2OH$, $-CH_2CH(CH_3)OH$ and $-CH_2CH_2OCH_2CH_2OH$; and
(ii) $R^3$ is selected from the group consisting of $-H$, $-CH_2CH_2OH$.

In a preferred embodiment, the amidation is conducted at a temperature of from about 80° C. to about 90° C. in the presence of an anhydrous alkaline catalyst. By processing in this temperature range, alkanolamides of the present invention and glycerin remain in the product. In contrast, when methyl esters or fatty acids are used in preparing alkanolamides, methanol or water, respectively, are distilled off, resulting in the loss of desirable unsaponifiables. The lower processing temperatures are also more compatible with, and maintain the potency of, antioxidants present in the unsaponifiables.

In a preferred embodiment, the effective concentration of alkanolamide ranges from about 0.5% to about 15.0% by weight.

In a preferred embodiment $R^2$ is $-CH_2CH_2OH$, and $R^3$ is $-H$.

In a preferred embodiment $R^2$ is $-CH_2CH_2OH$, and $R^3$ is $-CH_2CH_2OH$.

In a preferred embodiment $R^2$ is $-CH_2CH_2O-CH_2CH_2OH$, and $R^3$ is $-H$.

In a preferred embodiment $R^2$ is $-CH_2CH(CH_3)OH$, and $R^3$ is $-H$.

The following examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

EXAMPLES

Mild-processed shea butter is made according to the following procedure: 500.0 grams of nuts from the shea butter tree are cracked into small pieces and placed into a one-liter vat of water. The water is then heated to 100° C. As the temperature increases, an oil phase develops on the surface of the water. The temperature is held for about 2 hours, after which the oil is decanted and passed through filter paper. The resulting oil is mild-processed shea butter according to the present invention and may be used in making alkanolamides. It is rich in unsaponifiables, from about 7% to about 15% by weight.

Examples 5–8 are illustrative of the MPSB alkanolamides of the present invention. To the specified number of grams of alkanolamine (Examples 1–4) is added the specified number of grams of MPSB. This mass is heated to from about 80° C. to about 90° C. Thereafter, about 0.4% by weight of solid sodium methylate powder is added. The mass is held within the specified temperature range for a period of from about four to about six hours. Nothing is distilled off during this time. The amine value drops during this period and, after several hours, stabilizes. Once the amine value stabilizes, the reaction is held an additional hour and the reaction mass is cooled to ambient temperature. Important to the preparation of MPSB alkanolamides of the present invention is the low processing temperatures. This requires neither distillation of water or processing at high temperatures (e.g., from about 180° C. to about 190° C.).

Examples 5–8

Mild-Processed Shea Butter Alkanolamides

| Example | Alkanolamine Example | Alkanolamine Grams | MPSB Grams |
|---------|---------------------|--------------------|------------|
| 5 | Example 1 | 295.0 | 1450.0 |
| 6 | Example 2 | 525.0 | 1450.0 |
| 7 | Example 3 | 510.0 | 1450.0 |
| 8 | Example 4 | 370.0 | 1450.0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. An alkanolamide derived from shea butter conforming to the structure:

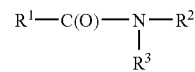

wherein
(i) $R^1$ is derived from shea butter and comprises
from about 0.1 to about 2.0% by weight $C_{11}H_{23}$;
from about 0.5 to about 2.0% by weight $C_{13}H_{27}$;
from about 2.0 to about 6.0% by weight $C_{15}H_{31}$;
from about 25 to about 50% by weight $C_{17}H_{35}$; and
from about 40.0 to about 60.0% by weight $C_{17}H_{33}$;
(ii) $R^2$ is selected from the group consisting of $-CH_2CH_2OH$, $-CH_2CH(CH_3)OH$ and $-CH_2CH_2OCH_2CH_2OH$; and
(iii) $R^3$ is selected from the group consisting of $-H$ and $-CH_2CH_2OH$.

2. An alkanolamide of claim 1 wherein $R^1$ is $-CH_2CH_2OH$, and $R^2$ is $-H$.

3. An alkanolamide of claim 1 wherein $R^1$ is $-CH_2CH_2OH$, and $R^2$ is $-CH_2CH_2OH$.

4. An alkanolamide of claim 1 wherein $R^1$ is $-CH_2CH_2O-CH_2CH_2OH$, and $R^2$ is $-H$.

5. An alkanolamide of claim 1 wherein $R^1$ is $-CH_2CH(CH_3)OH$, and $R^2$ is $-H$.

6. An alkanolamide according to claim 1 obtained by the amidation reaction of
(a) an alkanolamine conforming to the following structure:

wherein
(i) $R^2$ is selected from the group consisting of —$CH_2CH_2OH$, —$CH_2CH(CH_3)OH$ and —$CH_2CH_2OCH_2CH_2OH$; and
(ii) $R^3$ is selected from the group consisting of —H, —$CH_2CH_2OH$; and (b) a shea butter comprising from about 0.1 to about 2.0% by weight $C_{11}H_{23}$;

from about 0.5 to about 2.0% by weight $C_{13}H_{27}$;

from about 2.0 to about 6.0% by weight $C_{15}H_{31}$;

from about 25 to about 50% by weight $C_{17}H_{35}$; and from about 40.0 to about 60.0% by weight $C_{17}H_{33}$.

7. An alkanolamide of claim 6 wherein $R^2$ is —$CH_2CH_2OH$, and $R^3$ is —H.

8. An alkanolamide of claim 6 wherein $R^2$ is —$CH_2CH_2OH$, and $R^3$ is —$CH_2CH_2OH$.

9. An alkanolamide of claim 6 wherein $R^2$ is —$CH_2CH_2O$—$CH_2CH_2OH$, and $R^3$ is —H.

10. An alkanolamide of claim 6 wherein $R^2$ is —$CH_2CH(CH_3)OH$, and $R^3$ is —H.

11. An alkanolamide of claim 6 wherein the amidation is conducted at a temperature of from about 80° C. to about 90° C. in the presence of an anhydrous alkaline catalyst.

12. An alkanolamide of claim 11 wherein $R^2$ is —$CH_2CH_2OH$, and $R^3$ is —H.

13. An alkanolamide of claim 11 wherein $R^2$ is —$CH_2CH_2OH$, and $R^3$ is —$CH_2CH_2OH$.

14. An alkanolamide of claim 11 wherein $R^2$ is —$CH_2CH_2O$—$CH_2CH_2OH$, and $R^3$ is —H.

15. An alkanolamide of claim 11 wherein $R^2$ is —$CH_2CH(CH_3)OH$, and $R^3$ is —H.

16. A process for treating hair and skin with an effective concentration of an alkanolamide made by the amidation reaction of shea butter and an alkanolamine conforming to the following structure:

wherein
(i) $R^2$ is selected from the group consisting of —$CH_2CH_2OH$, —$CH_2CH(CH_3)OH$ and —$CH_2CH_2OCH_2CH_2OH$; and
(ii) $R^3$ is selected from the group consisting of —H, —$CH_2CH_2OH$.

17. A process of claim 16 wherein $R^2$ is —$CH_2CH_2OH$, and $R^3$ is —H.

18. A process of claim 16 wherein $R^2$ is —$CH_2CH_2OH$, and $R^3$ is —$CH_2CH_2OH$.

19. A process of claim 16 wherein $R^2$ is —$CH_2CH_2O$—$CH_2CH_2OH$, and $R^3$ is —H.

20. A process of claim 16 wherein $R^2$ is —$CH_2CH(CH_3)OH$, and $R^3$ is —H.

21. A process of claim 16 wherein the amidation is conducted at a temperature of from about 80° C. to about 90° C. in the presence of an anhydrous alkaline catalyst.

22. A process of claim 21 wherein $R^2$ is —$CH_2CH_2OH$, and $R^3$ is —H.

23. A process of claim 21 wherein $R^2$ is —$CH_2CH_2OH$, and $R^3$ is —$CH_2CH_2OH$.

24. A process of claim 21 wherein $R^2$ is —$CH_2CH_2O$—$CH_2CH_2OH$, and $R^3$ is —H.

25. A process of claim 21 wherein $R^2$ is —$CH_2CH(CH_3)OH$, and $R^3$ is —H.

26. A process of claim 16 wherein the effective concentration of the alkanolamide ranges from about 0.5% to about 15.0% by weight.

27. A process of claim 26 wherein $R^2$ is —$CH_2CH_2OH$, and $R^3$ is —H.

28. A process of claim 26 wherein $R^2$ is —$CH_2CH_2OH$, and R is —$CH_2CH_2OH$.

29. A process of claim 26 wherein $R^2$ is —$CH_2CH_2O$—$CH_2CH_2OH$, and $R^3$ is —H.

30. A process of claim 26 wherein $R^3$ is —$CH_2CH(CH_3)OH$, and $R^3$ is —H.

31. An alkanolamide of claim 1 where the shea butter is mild-processed.

32. A process of claim 16 where the shea butter is mild-processed.

* * * * *